US00PP23513P2

(12) United States Plant Patent
Korlipara

(10) Patent No.: US PP23,513 P2
(45) Date of Patent: Apr. 2, 2013

(54) ***ECHINACEA* PLANT NAMED 'SECRET PRIDE'**

(50) Latin Name: ***Echinacea* hybrid**
Varietal Denomination: Secret Pride

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 68 days.

(21) Appl. No.: 13/200,419

(22) Filed: Sep. 23, 2011

(51) Int. Cl.
*A01H 5/00* (2006.01)

(52) U.S. Cl. ..... Plt./428

(58) Field of Classification Search ..... Plt./428
See application file for complete search history.

*Primary Examiner* — Howard Locker

(74) *Attorney, Agent, or Firm* — Klarquist Sparkman, LLP

(57) ABSTRACT

A new and distinct *Echinacea* plant named 'Secret Pride' characterized by white ray florets, enlarged light yellow disc florets forming an anemone-type inflorescence, compact habit with multiple crowns, and excellent vigor.

1 Drawing Sheet

Botanical denomination: *Echinacea* hybrid.

Variety designation: 'Secret Pride'.

The present invention relates to a new and distinct cultivar of *Echinacea* and given the cultivar name 'Secret Pride'. *Echinacea* is in the family *Asteraceae*. This new cultivar is a third generation seeding originating from a planned breeding program using *Echinacea purpurea* 'Razzmatazz' (U.S. Plant Pat. No. 13,894) as the seed parent in the original cross and unnamed proprietary, unreleased interspecific hybrids (*Echinacea paradoxa*×*Echinacea purpurea*) for the pollen parent. The exact parents of this selection are unknown, unnamed, proprietary plants.

Compared to *Echinacea purpurea* 'Razzmatazz' (U.S. Plant Pat. No. 13,894), the seed parent in the original breeding line, the new variety has a much more compact habit and has white rather than pink inflorescences.

Compared to *Echinacea* 'Meringue' (U.S. Plant Pat. No. 20,537), the new cultivar is taller with a much larger inflorescence and longer ray florets.

This new *Echinacea* cultivar is distinguished by:

1. white ray florets,
2. enlarged light yellow disc florets forming an anemone-type inflorescence,
3. compact habit with multiple crowns, and
4. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows *Echinacea* 'Secret Pride' in full bloom as a one-year-old in the field in full sun in July in Canby, Oreg.

DETAILED PLANT DESCRIPTION

The following is a detailed description of the new *Echinacea* cultivar based on observations of a 2-year-old specimens growing in the ground in the trial beds in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, 5$^{th}$ edition.

Plant:

*Type*.—Herbaceous perennial.
*Hardiness*.—USDA Zones 4 to 9.
*Size*.—Grows to about 75 cm wide and 65 cm tall to top of inflorescences.
*Form*.—Basal clump, with about 60 stems from the base.
*Vigor*.—Excellent.
*Roots*.—Fibrous, with many downward growing and few laterals, ivory in color, Yellow White 158D, roots develop easily from cuttings from the crown.

Stem (flowering):

*Type*.—Ascending, with 0 to 5 flowering branches off the main flowering stems.
*Size*.—To 58 cm tall to a terminal inflorescence and 6 mm wide at base.
*Internode length*.—5 cm to 9 cm.
*Surface texture*.—Strigose.
*Color*.—Yellow Green N144A.

Leaf (basal):

*Type*.—Simple.
*Shape*.—Ovate to broadly lanceolate.
*Arrangement*.—Basal.
*Blade size*.—Grows to 13 cm long and 6 cm wide.
*Margins*.—Sparsely serrate.
*Apex*.—Acute.
*Base*.—Attenuate.
*Surface texture*.—Strigose on both sides.
*Venation*.—Pinnate.
*Color*.—Topside, Green 137A, bottom side closest to Yellow Green 147B with vein Yellow Green 146C.

*Petiole description*.—Grows to 14 cm long and 2 mm wide, glabrous, Yellow Green 146C.

Leaf (stem):

*Type*.—Simple.

*Shape*.—Lanceolate.

*Arrangement*.—Alternate.

*Blade size*.—Grows to 13 cm long and 3.6 cm wide.

*Margins*.—Sparsely serrate.

*Apex*.—Acuminate.

*Base*.—Attenuate.

*Surface texture*.—Strigose on both sides.

*Venation*.—Pinnate, with 3 main veins from the base.

*Color*.—Topside, Yellow Green 147A with veins Yellow Green 146C, bottom side closest to Yellow Green 147B with veins Yellow Green 146C.

*Petiole description*.—On lowermost leaves only, clasping, grows to 2 cm long and 5 mm wide above the clasp, strigose, Yellow Green 146C.

Inflorescence:

*Type*.—Composite on terminal stalked heads.

*Number of flowering stems from the ground*.—About 60.

*Flowering stem*.—Grows to 63 cm tall from the base of the plant to the terminal inflorescence and can grow to 15 cm long from the top stem leaf to the base of an inflorescence; branched, with 1 to 3 inflorescences per stem; diameter growing to 6.5 mm wide near the inflorescence; strigose; Yellow Green 146C.

*Size*.—Grows to 86 mm wide and 35 mm deep as disc enlarges.

*Form*.—Ray florets held horizontally, mature disc is conic.

*Phyllaries*.—In 4 leafy series, area 3 cm wide and 10 mm deep, lobes lanceolate in shape, reflexed, grow to 15 mm long and 2.5 mm wide, Yellow Green 147B, margins strigose, tip acute, strigose on both sides.

*Receptacle*.—Grows to 11 mm wide and 18 mm deep, White 155A.

*Immature inflorescence*.—Grows to 3 cm wide and 2 cm deep, disc area 15 mm wide and Yellow Green 144A, ray florets held slightly upright and rolled up so only the back color shows, Yellow 4D with the tips Yellow Green N144D.

*Ray florets*.—Without pistil or stamen, about 22 in number, grow to 45 mm long and 9 mm wide, oblanceolate with the tip two to three toothed (each acute), entire margins, base attenuate, glabrous on both sides; topside White 155A, bottom side White 155A with Yellow Green N144D on tips and veins.

*Disc*.—Flat becoming conic, becoming 32 mm deep and 40 mm wide with maturity, overall color is Yellow 4D.

*Disc florets*.—About 250 in number, each with 1 pistil and 4 stamen, grow to 15 mm long and 8 mm wide, each with one persistent, very stiff linear bract (12 mm long with the top 2 mm colored Yellow Orange 21A on tip then Yellow Green 144A in middle, then White 155B on bottom ⅓); showy corollas to grow to 12 mm long and 10 mm wide, tubular on the bottom with the lobes spread out like a fan or fan-like on one side and limb-like on the other, 5 lobes, glabrous on both sides, back side color Green Yellow 1D on lobes and Yellow Green 147C on tube, inside color Green White 157D; pistil 7 mm long, ovary 3 mm long, White NN155D, style 6 mm long Yellow Green 149D, 2-branched stigma spreading, Yellow Orange 18B; stamen 5 mm long, anthers 2 mm long and Greyed Orange 166A, filaments 3 mm long, White 155A, no pollen.

*Bloom period*.—July through October in Canby, Oreg.

*Fragrance*.—Excellent, floral.

*Lastingness*.—Each inflorescence lasts about three weeks in Canby, Oreg.

Seeds: 0 to 3 per inflorescence, each 4 mm long and 2.5 mm wide, oval, Grey Brown N199A.

*Fertility*.—Poor.

Disease and pests: *Echinacea* are susceptible to leaf miners, powdery mildew, bacterial spots, and gray mold. None of these have been observed on plants grown under commercial conditions in Canby, Oreg. No resistance is known.

I claim:

1. A new and distinct *Echinacea* plant as herein illustrated and described.

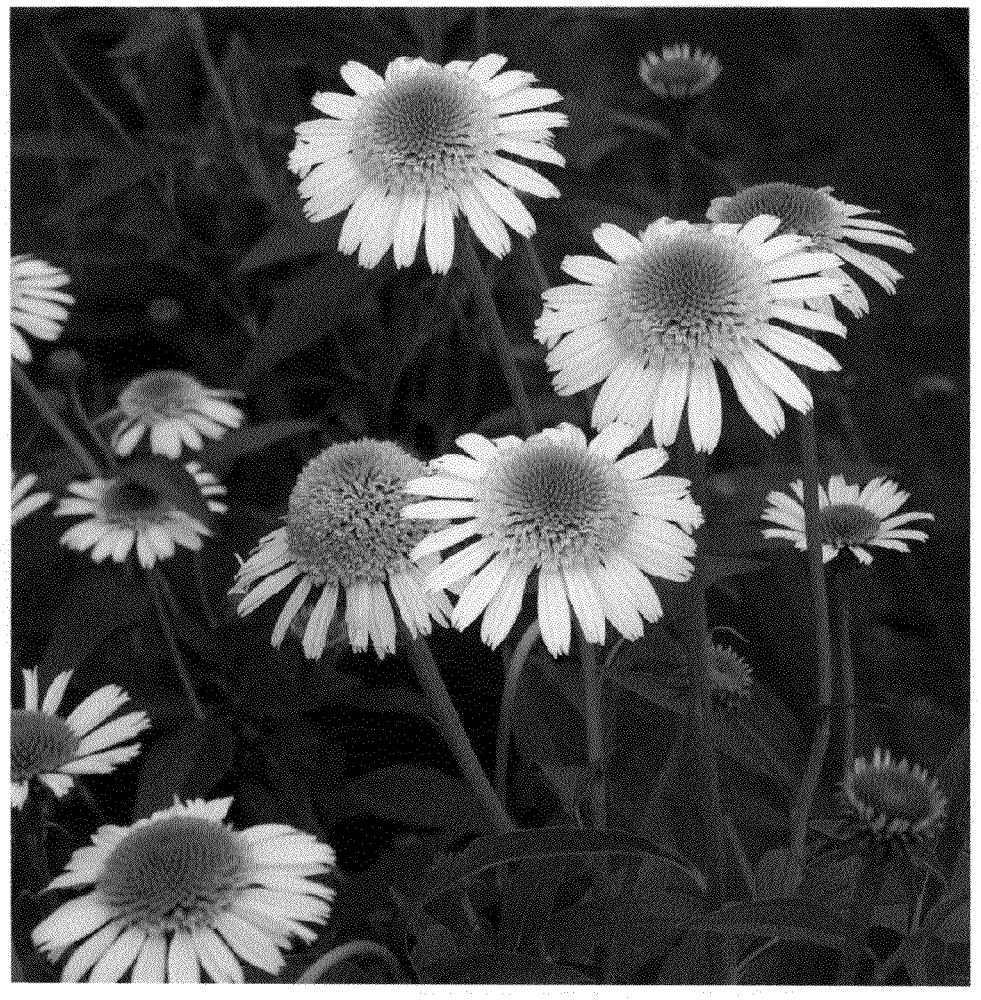

* * * * *